(12) United States Patent
Xu

(10) Patent No.: US 9,657,186 B2
(45) Date of Patent: May 23, 2017

(54) OPAQUE INKS AND APPLICATIONS THEREOF

(75) Inventor: Pingyong Xu, Valencia, CA (US)

(73) Assignee: 3D Systems, Inc., Rock Hill, SC (US)

( * ) Notice: Subject to any disclaimer, the term of this patent is extended or adjusted under 35 U.S.C. 154(b) by 113 days.

(21) Appl. No.: 13/596,670

(22) Filed: Sep. 13, 2012

(65) Prior Publication Data

US 2014/0072712 A1   Mar. 13, 2014

(51) Int. Cl.
| | |
|---|---|
| A61C 11/00 | (2006.01) |
| A61C 13/00 | (2006.01) |
| A61C 13/087 | (2006.01) |
| A61C 13/09 | (2006.01) |
| A61C 13/34 | (2006.01) |
| B29C 67/00 | (2017.01) |
| B33Y 70/00 | (2015.01) |
| C09D 11/101 | (2014.01) |
| C09D 11/34 | (2014.01) |

(52) U.S. Cl.
CPC ............ *C09D 11/101* (2013.01); *A61C 11/00* (2013.01); *A61C 13/0019* (2013.01); *A61C 13/087* (2013.01); *A61C 13/09* (2013.01); *A61C 13/34* (2013.01); *C09D 11/34* (2013.01); *B29C 67/0055* (2013.01); *B33Y 70/00* (2014.12)

(58) Field of Classification Search
CPC ... C09D 11/101; C09D 11/34; B29C 67/0055; B33Y 70/00; A61C 11/00; A61C 13/0019; A61C 13/087; A61C 13/09; A61C 13/34
USPC ............... 523/160, 161; 524/198, 313, 480; 525/123, 455; 264/401
See application file for complete search history.

(56) References Cited

U.S. PATENT DOCUMENTS

| | | |
|---|---|---|
| 2,409,712 A | 10/1946 | Schweitzer |
| 3,012,991 A | 12/1961 | Schultheis et al. |
| 3,653,932 A | 4/1972 | Berry et al. |
| 3,796,678 A | 3/1974 | Bartizal |
| 3,963,710 A | 6/1976 | Aufdermarsh, Jr. |
| 4,011,311 A | 3/1977 | Noomen et al. |
| 4,293,470 A | 10/1981 | Cuscurida |
| 4,297,501 A | 10/1981 | Becker et al. |
| 4,334,032 A | 6/1982 | Patton, Jr. et al. |
| 4,381,403 A | 4/1983 | Falcone et al. |
| 4,390,369 A | 6/1983 | Merritt et al. |
| 4,484,948 A | 11/1984 | Merritt et al. |
| 4,501,915 A | 2/1985 | McCoy |
| 4,537,960 A | 8/1985 | Merger et al. |
| 4,555,357 A | 11/1985 | Kausga et al. |
| 4,665,146 A | 5/1987 | Tortorello et al. |
| 4,684,956 A | 8/1987 | Ball |
| 4,810,820 A | 3/1989 | Slack et al. |
| 4,830,671 A | 5/1989 | Frihart et al. |
| 4,851,045 A | 7/1989 | Taniguchi |
| 4,889,506 A | 12/1989 | Connolly et al. |
| 4,889,560 A | 12/1989 | Jaeger et al. |
| 4,889,761 A | 12/1989 | Titterington et al. |
| 5,006,170 A | 4/1991 | Schwarz et al. |
| 5,141,749 A | 8/1992 | Herting et al. |
| 5,151,120 A | 9/1992 | You et al. |
| 5,162,490 A | 11/1992 | Drawert et al. |
| 5,195,430 A | 3/1993 | Rise |
| 5,208,034 A | 5/1993 | Herting et al. |
| 5,221,335 A | 6/1993 | Williams et al. |
| 5,286,288 A | 2/1994 | Tobias et al. |
| 5,372,852 A | 12/1994 | Titterington et al. |
| 5,389,720 A | 2/1995 | Markusch et al. |
| 5,389,958 A | 2/1995 | Bui et al. |
| 5,421,868 A | 6/1995 | Ayalia-Esquilin et al. |
| 5,496,879 A | 3/1996 | Griebel et al. |
| 5,507,864 A | 4/1996 | Jaeger et al. |
| 5,574,078 A | 11/1996 | Elwaki |
| 5,593,486 A | 1/1997 | Oliver et al. |
| 5,597,856 A | 1/1997 | Yu et al. |
| 5,607,501 A | 3/1997 | Fujioka |
| 5,621,022 A | 4/1997 | Jaeger et al. |
| 5,780,528 A | 7/1998 | Titterington et al. |
| 5,881,648 A | 3/1999 | Pavlin |
| 5,902,841 A | 5/1999 | Jaeger et al. |
| 5,919,839 A | 7/1999 | Titterington et al. |
| 6,133,353 A | 10/2000 | Bui et al. |
| 6,288,141 B1 | 9/2001 | Malhota |
| 6,395,811 B1 | 5/2002 | Nguyen et al. |
| 6,406,531 B1 | 6/2002 | Bui et al. |
| 6,492,458 B1 | 12/2002 | Pavlin |
| 6,713,125 B1 * | 3/2004 | Sherwood et al. ........... 427/157 |
| 6,841,589 B2 | 1/2005 | Schmidt et al. |

(Continued)

FOREIGN PATENT DOCUMENTS

| | | |
|---|---|---|
| DE | 42 05 636 | 8/1993 |
| DE | 42 05 713 | 8/1993 |
| EP | 0 187 352 | 7/1986 |
| EP | 0 206 286 | 12/1986 |
| EP | 0 819 739 | 1/1998 |

(Continued)

OTHER PUBLICATIONS

Odian, George, Principles of Polymerization, Third Edition, 1991, pp. 29-33.*
PCT International Search Report for International Application No. PCT/US2013/056158 (5 pages).
PCT Written Opinion of International Search Report for International Application No. PCT/US2013/056158 (5 pages).

*Primary Examiner* — Patrick Niland

(57) ABSTRACT

In one aspect, inks for use with a three dimensional printing system are described herein. In some embodiments, an ink for use in a three dimensional printing system comprises about 10-95 weight % polymerizable component and about 3-25 weight % non-reactive wax component, wherein the ink when cured has a $T_g$ greater than the melting point of the non-reactive wax component.

20 Claims, 2 Drawing Sheets

(56) References Cited

U.S. PATENT DOCUMENTS

| | | |
|---|---|---|
| 6,860,930 B2 | 3/2005 | Wu et al. |
| 6,946,025 B2 | 9/2005 | Wu et al. |
| 7,104,773 B2 | 9/2006 | Maekawa et al. |
| 7,183,335 B2 * | 2/2007 | Napadensky ....... B29C 67/0059 522/173 |
| 7,378,460 B2 | 5/2008 | Schmidt et al. |
| 7,381,254 B2 | 6/2008 | Wu et al. |
| 7,531,117 B2 | 5/2009 | Ederer et al. |
| 7,736,578 B2 | 6/2010 | Ederer |
| 7,767,130 B2 | 8/2010 | Elsner et al. |
| 7,927,539 B2 | 4/2011 | Ederer |
| 7,955,537 B2 | 6/2011 | Ederer et al. |
| 7,967,902 B2 | 6/2011 | Banning et al. |
| 8,021,730 B2 | 9/2011 | Tsou et al. |
| 8,029,610 B2 | 10/2011 | Banning et al. |
| 8,070,866 B2 | 12/2011 | Banning et al. |
| 2002/0064759 A1 * | 5/2002 | Durbin .................. A61C 9/00 433/213 |
| 2003/0092820 A1 | 5/2003 | Schmidt |
| 2005/0080163 A1 * | 4/2005 | Schmidt et al. ............. 523/160 |
| 2006/0131770 A1 * | 6/2006 | Dierkes et al. ................. 264/16 |
| 2011/0152397 A1 | 6/2011 | Breton |

FOREIGN PATENT DOCUMENTS

| | | |
|---|---|---|
| EP | 0 844 287 | 5/1998 |
| EP | 0 869 161 | 10/1998 |
| GB | 2 294 939 | 5/1996 |
| GB | 2336594 | 10/1999 |
| SU | 438664 | 8/1974 |
| WO | WO 94/04619 | 3/1994 |
| WO | WO 94/14902 | 7/1994 |
| WO | WO 96/02399 | 2/1996 |
| WO | WO 96/02446 | 2/1996 |
| WO | WO 96/10051 | 4/1996 |
| WO | WO 97/12003 | 4/1997 |
| WO | WO 98/26013 | 6/1998 |
| WO | 99/07772 | 2/1999 |
| WO | WO 00/11092 | 3/2000 |
| WO | 03/028985 | 4/2003 |
| WO | 03/029365 | 5/2003 |
| WO | 2012/121884 | 9/2012 |

* cited by examiner

OPAQUE INKS AND APPLICATIONS THEREOF

FIELD

The present invention relates to inks and, in particular, to opaque inks for use with three dimensional (3D) printing systems.

BACKGROUND

Commercially available three dimensional printers, such as the ProJet™ 3D Printers manufactured by 3D Systems of Rock Hill, S.C., use inks, which are also known as build materials, that are jetted through a print head as a liquid to form various three-dimensional objects or parts. Other three dimensional printing systems also use an ink that is jetted through a print head. In some instances, the ink is solid at ambient temperatures and converts to liquid at elevated jetting temperatures. In other instances, the ink is liquid at ambient temperatures.

Many inks provide printed parts that are transparent or translucent at room temperature (about 25° C.). However, it is sometimes desirable to produce opaque rather than transparent or translucent printed parts. Some applications, including some dental modeling applications, require opaque materials. Opaque materials, in some instances, can be examined more easily and more accurately than translucent or transparent materials. Similarly, automatic surface scanning methods sometimes require or prefer the use of opaque materials.

In addition, the use of pigments to render inks opaque can present manufacturing challenges, such as the need for continual circulation of pigmented inks and/or frequent cleaning or replacement of print heads.

SUMMARY

In one aspect, inks for use with a 3D printer are described herein which, in some embodiments, may offer one or more advantages over prior inks. In some embodiments, for example, an ink described herein provides printed parts that are opaque at room temperature, thereby providing finished parts that are useful in various modeling and engineering applications. Further, in some embodiments, an ink described herein provides opaque printed parts without the use of pigments such as inorganic pigments, thereby simplifying the printing process and extending print head lifetime.

In some embodiments, an ink for use in a 3D printing system comprises about 10-95 weight % polymerizable component and about 3-25 weight % non-reactive wax component, based on the total weight of the ink. In some embodiments, an ink further comprises about 1-10 weight % oil. Moreover, in some embodiments, an ink for use in a 3D printing system comprises about 10-95 weight % polymerizable component and about 3-25 weight % non-reactive wax component, wherein the ink when cured has a glass transition temperature ($T_g$) greater than the melting point of the non-reactive wax component. The ink, in some embodiments, further comprises an oil.

Moreover, in some embodiments, an ink described herein further comprises at least one dye. In addition, in some embodiments, an ink described herein further comprises an additive that promotes rapid curing of the surface of the ink and/or promotes the production of a tack free finished part. In some embodiments, an ink described herein further comprises one or more additives selected from the group consisting of photoinitiators, inhibitors, stabilizing agents, sensitizers, and combinations thereof.

Further, in some embodiments, an ink described herein is not pigmented. In addition, in some embodiments, a pigment-free or substantially pigment-free ink described herein is opaque at room temperature when cured.

In another aspect, compositions are described herein. In some embodiments, a composition comprises a three dimensionally printed article comprising an ink, the ink comprising about 10-95 weight % polymerizable component and about 3-25 weight % non-reactive wax component. In some embodiments, the ink when cured has a $T_g$ greater than the melting point of the non-reactive wax component. Moreover, in some embodiments, an ink described herein further comprises about 1-10 weight % oil.

In another aspect, methods of printing a three dimensional article are described herein. In some embodiments, a method of printing a 3D article comprises selectively depositing layers of a fluid ink to form the 3D article on a substrate, the ink comprising about 10-95 weight % polymerizable component and about 3-25 weight % non-reactive wax component. In some embodiments, the ink when cured has a $T_g$ greater than the melting point of the non-reactive wax component. Moreover, in some embodiments, the ink of a composition described herein further comprises about 1-10 weight % oil.

In addition, in some embodiments, the layers of the ink are deposited according to an image of the 3D article in a computer readable format and/or according to preselected computer aided design (CAD) parameters. Moreover, in some embodiments, a method described herein further comprises curing the layers of ink. In some embodiments, a method described herein further comprises heating the 3D article to a temperature greater than the melting point of the non-reactive wax component. In addition, in some embodiments, a method further comprises cooling the 3D article to room temperature. Cooling, in some embodiments, is carried out rapidly.

These and other embodiments are described in greater detail in the detailed description which follows.

DETAILED DESCRIPTION

Figure 1:
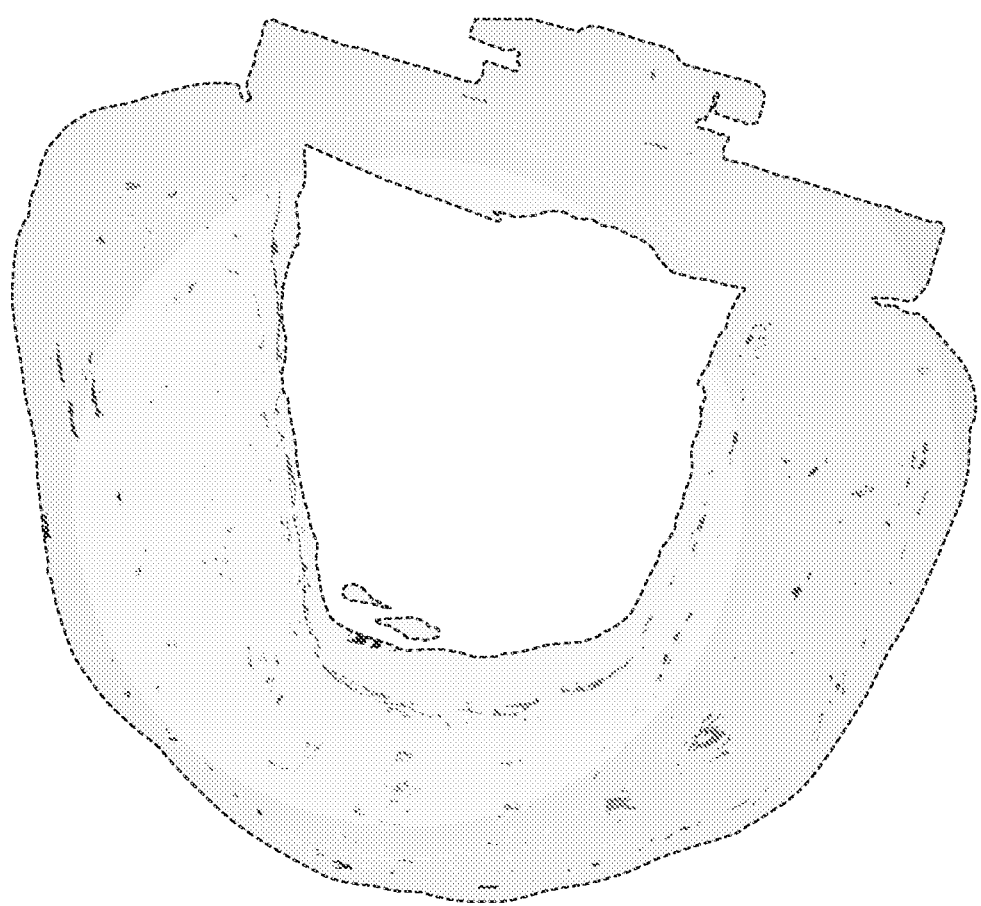
FIG. 1 illustrates the optical scanning properties of a printed article formed from an ink that is not according to an embodiment described herein.

Embodiments described herein can be understood more readily by reference to the following detailed description, examples, and drawings. Elements, apparatus and methods described herein, however, are not limited to the specific embodiments presented in the detailed description, examples, and drawings. It should be recognized that these embodiments are merely illustrative of the principles of the present invention. Numerous modifications and adaptations will be readily apparent to those of skill in the art without departing from the spirit and scope of the invention.

In addition, all ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, or 4.7 to 10.0, or 3.6 to 7.9.

The terms "three dimensional printing system," "three dimensional printer," "printing," and the like generally describe various solid freeform fabrication techniques for making three dimensional objects by selective deposition, jetting, fused deposition modeling, multijet modeling, and other techniques now known in the art or that may be known in the future that use a build material or ink to fabricate the three dimensional object.

I. Inks

In one aspect, inks are described herein. An ink described herein, in some embodiments, may offer one or more advantages over prior inks. In some embodiments, for example, an ink described herein provides printed parts that are opaque at room temperature, thereby providing finished parts that are useful in various modeling and engineering applications such as dental applications. Further, in some embodiments, an ink described herein provides opaque printed parts without the use of pigments such as inorganic pigments, thereby simplifying the printing process and/or extending print head lifetime. Adding pigments to inks often requires special handling of the inks for ink jet printing, such as constantly recirculating the inks so that added pigments do not settle or separate from the inks. In addition, not intending to be bound by theory, it is believed that the pigments of some prior inks can accumulate near print head orifices and thereby disturb or interrupt the printing process. The presence of pigments in inks, particularly inorganic pigments, can also reduce effective print head lifetimes and/or increase the amount of repair or replacement of print heads required. Extending the effective lifetime of ink jet print heads, in some embodiments, can also facilitate wide-format printing. In some embodiments described herein, a pigment-free, UV-curable opaque ink for use with 3D printing systems is provided.

In some embodiments, an ink for use in a 3D printing system comprises about 10-95 weight % polymerizable component and about 3-25 weight % non-reactive wax component, based on the total weight of the ink. Further, in some embodiments, the ink when cured has a $T_g$ greater than the melting point of the non-reactive wax component. In addition, in some embodiments, an ink described herein further comprises an oil, including in an amount of about 1-10 weight %, based on the total weight of the ink. Moreover, in some embodiments, an ink described herein further comprises at least one dye. In addition, in some embodiments, an ink described herein further comprises an additive that promotes rapid curing of the surface of the ink and/or promotes the production of a tack free finished part. In some embodiments, an ink described herein further comprises one or more additives selected from the group consisting of photoinitiators, inhibitors, stabilizing agents, sensitizers, and combinations thereof. Further, in some embodiments, an ink described herein is not pigmented. In addition, in some embodiments, a pigment-free or substantially pigment-free ink described herein is opaque at room temperature when cured.

Inks described herein comprise about 10-95 weight % polymerizable component, based on the total weight of the ink. In some embodiments, an ink comprises about 20-80 weight % polymerizable component, about 30-70 weight % polymerizable component, or about 70-90 weight % polymerizable component. Moreover, a polymerizable component, in some embodiments, comprises a component that can be polymerized or cured to provide a printed 3D article or object. Polymerizing or curing can be carried out in any manner not inconsistent with the objectives of the present invention. In some embodiments, for instance, polymerizing or curing comprises irradiating with electromagnetic radiation having sufficient energy to initiate a polymerization or cross-linking reaction. For instance, in some embodiments, ultraviolet (UV) radiation can be used.

Further, any polymerizable component not inconsistent with the objectives of the present invention may be used. In some embodiments, a polymerizable component comprises a monomeric chemical species, such as a chemical species having one or more functional groups or moieties that can react with the same or different functional groups or moities of another monomeric chemical species to form one or more covalent bonds, such as in a polymerization reaction. A polymerization reaction, in some embodiments, comprises a free radical polymerization, such as that between points of unsaturation, including points of ethylenic unsaturation. In some embodiments, a polymerizable component comprises at least one ethyleneically unsaturated moiety, such as a vinyl group or allyl group. In some embodiments, a polymerizable component comprises an oligomeric chemical species capable of undergoing additional polymerization, such as through one or more points of unsaturation as described herein. In some embodiments, a polymerizable component comprises one or more monomeric chemical species and one or more oligomeric chemical species described herein. A monomeric chemical species and/or an oligomeric chemical species described herein can have one polymerizable moiety or a plurality of polymerizable moieties.

In some embodiments, a polymerizable component comprises one or more photo-polymerizable or photo-curable chemical species. A photo-polymerizable chemical species, in some embodiments, comprises a UV-polymerizable chemical species. In some embodiments, a polymerizable component is photo-polymerizable or photo-curable at wavelengths ranging from about 300 nm to about 400 nm. Alternatively, in some embodiments, a polymerizable component is photo-polymerizable at visible wavelengths of the electromagnetic spectrum.

In some embodiments, a polymerizable component described herein comprises one or more species of (meth) acrylates. As used herein, the term "(meth)acrylate" includes acrylate or methacrylate or mixtures or combinations thereof. In some embodiments, a polymerizable component comprises a urethane (meth)acrylate resin. In some embodiments, a UV polymerizable or curable urethane (meth) acrylate resin can comprise any methacrylate or acrylate resin which polymerizes in the presence of a free radical photoinitiator, is thermally stable in an exposed state for at least one week at the jetting temperature and for at least 4 weeks in an enclosed state, and/or has a boiling point greater than the jetting temperature. In some embodiments, a polymerizable component has a flash point above the jetting temperature.

Urethane (meth)acrylates suitable for use in inks described herein, in some embodiments, can be prepared in a known manner, typically by reacting a hydroxyl-terminated urethane with acrylic acid or methacrylic acid to give the corresponding urethane (meth)acrylate, or by reacting an isocyanate-terminated prepolymer with hydroxyalkyl acrylates or methacrylates to give the urethane (meth)acrylate. Suitable processes are disclosed, inter alia, in EP-A 114 982 and EP-A 133 908. The weight average molecular weight of such (meth)acrylate oligomers is generally in the range from about 400 to 10,000, or from about 500 to 7,000. Urethane (meth)acrylates are also commercially available from the SARTOMER Company under the product names CN980, CN981, CN975 and CN2901, or from Bomar Specialties Co. (Winsted, Conn.) under the product name BR-741. In some embodiments described herein, a urethane (meth)acrylate oligomer has a viscosity ranging from about 140,000 cP to about 160,000 cP at about 50° C. or from about 125,000 cP to about 175,000 cP at about 50° C. when measured in a manner consistent with ASTM D2983. In some embodiments described herein, a urethane (meth)acrylate oligomer has a viscosity ranging from about 100,000 cP to about 200,000 cP at about 50° C. or from about 10,000 cP to about 300,000 cP at about 50° C. when measured in a manner consistent with ASTM D2983.

In some embodiments, a polymerizable component comprises one or more low molecular weight materials, such as methacrylates, dimethacrylates, triacrylates, and diacrylates, which can be used in a variety of combinations. In some embodiments, for example, a polymerizable component comprises one or more of tetrahydrofurfuryl methacrylate, triethylene glycol dimethacrylate, 2-phenoxyethyl methacrylate, lauryl methacrylate, ethoxylated trimethylolpropane triacrylate, polypropylene glycol monomethacrylate, polyethylene glycol monomethacrylate, cyclohexane dimethanol diacrylate, and tridecyl methacrylate.

In some embodiments, a polymerizable component comprises diacrylate and/or dimethacrylate esters of aliphatic, cycloaliphatic or aromatic diols, including 1,3- or 1,4-butanediol, neopentyl glycol, 1,6-hexanediol, diethylene glycol, triethylene glycol, tetraethylene glycol, polyethylene glycol, tripropylene glycol, ethoxylated or propoxylated neopentyl glycol, 1,4-dihydroxymethylcyclohexane, 2,2-bis (4-hydroxycyclohexyl)propane or bis(4-hydroxycyclohexyl)methane, hydroquinone, 4,4'-dihydroxybiphenyl, bisphenol A, bisphenol F, bisphenol S, ethoxylated or propoxylated bisphenol A, ethoxylated or propoxylated bisphenol F or ethoxylated or propoxylated bisphenol S.

A polymerizable component, in some embodiments, comprises one or more tri(meth)acrylates. In some embodiments, tri(meth)acrylates comprise 1,1-trimethylolpropane triacrylate or methacrylate, ethoxylated or propoxylated 1,1,1-trimethlolpropanetriacrylate or methacrylate, ethoxylated or propoxylated glycerol triacrylate, pentaerythritol monohydroxy triacrylate or methacrylate.

In some embodiments, a polymerizable component of an ink described herein comprises one or more higher functional acrylates or methacrylates such as dipentaerythritol monohydroxy pentaacrylate or bis(trimethylolpropane)tetraacrylate. In some embodiments, a (meth)acrylate of an ink has a molecular weight ranging from about 250 to 700.

In some embodiments, a polymerizable component comprises allyl acrylate, allyl methacrylate, methyl(meth)acrylate, ethyl(meth)acrylate, n-propyl(meth)acrylate, n-butyl (meth)acrylate, isobutyl(meth)acrylate, n-hexyl(meth) acrylate, 2-ethylhexyl(meth)acrylate, n-octyl(meth)acrylate, n-decyl(meth)acrylate and n-dodecyl(meth)acrylate, 2-hydroxyethyl(meth)acrylate, 2- and 3-hydroxypropyl(meth) acrylate, 2-methoxyethyl(meth)acrylate, 2-ethoxyethyl (meth)acrylate and 2- or 3-ethoxypropyl(meth)acrylate, tetrahydrofurfuryl methacrylate, 2-(2-ethoxyethoxy)ethyl acrylate, cyclohexyl methacrylate, 2-phenoxyethyl acrylate, glycidyl acrylate, isodecyl acrylate, or a combination thereof.

Additional non-limiting examples of species of polymerizable components useful in some embodiments described herein include the following: isobornyl acrylate (IBOA), commercially available from SARTOMER under the trade name SR 506A; isobornyl methacrylate, commercially available from SARTOMER under the trade name SR 423A; and triethylene glycol dimethacrylate, commercially available from SARTOMER under the trade name SR 205.

Inks described herein also comprise about 3-25 weight % non-reactive wax component, based on the total weight of the ink. In some embodiments, an ink comprises about 3-15 weight % or about 3-10 weight % non-reactive wax component. In some embodiments, an ink comprises about 5-15 weight % non-reactive wax component. Moreover, a non-reactive wax component of an ink described herein can comprise one or a plurality of non-reactive waxes. For reference purposes herein, a non-reactive wax is a wax that does not include a functional group or chemical moiety that can react with a functional group of a polymerizable component described herein in a polymerization or cross-linking reaction. For instance, in some embodiments, a non-reactive wax does not comprise an ethyleneically unsaturated moiety, such as a vinyl moiety or a (meth)acrylate moiety.

Any non-reactive wax not inconsistent with the objectives of the present invention may be used. Examples of suitable non-reactive waxes can be found in U.S. Pat. Nos. 6,133,353 and 6,395,811, the entireties of which are hereby incorporated by reference. In some embodiments, a non-reactive wax component comprises a heat-storage phase change (SPC) wax. In some embodiments, a non-reactive wax component comprises a hydrocarbon wax such as a hydrogenated wax, paraffin wax, microcrystalline wax, fatty ester wax or a mixture thereof.

In some embodiments, a non-reactive wax component comprises a urethane wax. In some embodiments, a non-reactive wax component comprises an inert linear urethane wax having the chemical formula $C_{18}H_{37}NRCOOC_nH_{(2n+1)}$ wherein n is an integer from 4 to 16, and R is H or C1-C20 alkyl. In some embodiments, R is H. In some embodiments, R is C1-C6 alkyl. In some embodiments, R is C1-C10 alkyl. In some embodiments, R is C1-C20 alkyl. In some embodiments, a non-reactive wax component comprises a mixture of C10, C12, C14, and C16 urethane waxes or a mixture of C10, C12, C16, and C18 urethane waxes, where Cn refers to the chain length on the oxygen side of the urethane moiety. In some embodiments, the chain lengths can be varied based on the desired viscosity and/or stiffness of the uncured ink; to obtain a cured ink having a desirable stiffness, break elongation, tensile modulus, stability at high temperature, and/or tensile strength; and/or to obtain an ink capable of being used in specific 3D printing systems to produce finished parts having desirable resolution and quality at a desirable speed. In some embodiments, a non-reactive wax component comprises a mixture of C10, C12, C14 and C16 or C10, C12, C16 and C18 urethane waxes in a weight ratio of about 1:1:1:1. In some embodiments, the weight ratio is within the range of about (1-10):(1-10):(1-10):(1-10). In some embodiments, the weight ratio is within the range of about (1-20):(1-20):(1-20):(1-20).

Non-limiting examples of a non-reactive wax component suitable for use in some embodiments of an ink described herein include ADS038 [1-dodecyl-N-octadecyl carbamate: $CH_3(CH_2)_{17}NHCOO(CH_2)_{11}CH_3$] and/or ADS043 [1-hexadecyl-N-octadecyl carbamate: $CH_3(CH_2)_{17}NHCOO(CH_2)_{15}CH_3$] waxes commercially available from American Dye Source, Inc. of Baie D'Urfe, Quebec, Canada.

Moreover, a non-reactive wax component described herein can have any melting point not inconsistent with the objectives of the present invention. In some embodiments, a non-reactive wax component has a melting point greater than about 60° C. or greater than about 70° C. In some embodiments, a non-reactive wax component has a melting point between about 65° C. and about 95° C., between about 65° C. and about 85° C., or between about 65° C. and about 75° C. In some embodiments, a non-reactive wax component has a melting point between about 70° C. and about 90° C., or between about 70° C. and about 80° C. In some embodiments, a non-reactive wax component has a melting point of about 75° C.

Inks described herein, in some embodiments, further comprise an oil. Any oil not inconsistent with the objectives of the present invention may be used. In some embodiments, an oil comprises an organic oil. An organic oil, in some embodiments, comprises a plant oil such as a vegetable oil or an essential oil. In some embodiments, an oil of an ink described herein comprises canola oil, castor oil, coconut oil, corn oil, cottonseed oil, olive oil, palm oil, peanut oil, safflower oil, soybean oil, sunflower oil, or a combination thereof. In other embodiments, an oil comprises a mineral oil. In some embodiments, an oil comprises a petrochemical oil. In some embodiments, an oil comprises a synthetic oil.

An oil of an ink described herein, in some embodiments, can at least partially dissolve a non-reactive wax of the ink. Further, in some embodiments, an oil of an ink described herein is liquid at standard temperature and pressure (STP) conditions. An oil can also have any molecular weight and viscosity not inconsistent with the objectives of the present invention. In some embodiments, for instance, an oil has a viscosity at 25° C. of about 10 cP to about 1000 cP when measured in a manner consistent with ASTM D2983. An oil, in some embodiments, has a viscosity at 25° C. of about 10 cP to about 100 cP, about 50 cP to about 500 cP, or about 50 cP to about 150 cP. In some embodiments, an oil has a molecular weight between about 200 and about 1000. An oil, in some embodiments, has a molecular weight between about 300 and about 500.

An oil can be present in an ink in any amount not inconsistent with the objectives of the present invention. In some embodiments, an oil is present in an amount ranging from about 1 weight percent to about 10 weight percent, based on the total weight of the ink. In some embodiments, an oil is present in an amount ranging from about 1 weight percent to about 5 weight percent or from about 3 weight percent to about 7 weight percent.

Inks described herein, in some embodiments, further comprise at least one dye. In some embodiments, an ink comprises a plurality of dyes, including dyes having differing absorption profiles. A dye, in some embodiments, comprises a chemical species that provides color to an ink and is soluble in the ink or in a component of the ink, such as a polymerizable component. In some embodiments, a dye comprises a liquid that provides color to an ink and disperses throughout the ink uniformly or substantially uniformly. A dye provides color to an ink, in some embodiments, by altering the light absorption or transmission profile of the ink. Further, in some embodiments, a dye described herein does not alter or does not substantially alter the light scattering profile of the ink. Any dye that is soluble in the ink and otherwise not inconsistent with the objectives of the present invention may be used. In some embodiments, a dye comprises an organic dye. Further, any combination of differing dyes not inconsistent with the objectives of the present invention may be used in an ink described herein, including dyes providing differing colors. Therefore, in some embodiments, an ink described herein can be used for full-color 3D printing of parts, including opaque parts.

A dye can be present in an ink in any amount not inconsistent with the objectives of the present invention. In some embodiments, a dye is present in an amount ranging from about 0.01 weight percent to about 2 weight percent, based on the total weight of the ink. In some embodiments, a dye is present in an amount ranging from about 0.01 weight percent to about 0.05 weight percent, from about 0.01 weight percent to about 0.1 weight percent, or from about 0.1 weight percent to about 0.5 weight percent.

An ink described herein, in some embodiments, further comprises an additive that promotes rapid curing of the surface of the ink and/or promotes the production of a tack free finished part. Any suitable additive for these purposes not inconsistent with the objectives of the present invention may be used. In some embodiments, an additive that promotes rapid curing of the surface of an ink and/or promotes the production of a tack free finished part comprises an amine modified oligomer. A non-limiting example of an amine modified oligomer useful in some embodiments described herein is Ebecryl 83, which is an amine modified acrylate oligomer commercially available from Cytec Corp. In some embodiments, an amine modified oligomer may be present in any amount not inconsistent with the objectives of the present invention. In some embodiments, an amine modified oligomer is present in an ink as described herein in an amount ranging from about 1 to about 10 weight percent, based on the total weight of the ink. In some embodiments, an amine modified oligomer is present in an amount less than about 3 weight percent.

In some embodiments, an ink described herein further comprises one or more additives selected from the group consisting of photoinitiators, inhibitors, stabilizing agents, sensitizers, and combinations thereof. For example, in some embodiments, an ink further comprises one or more photoinitiators. Any photoinitiator not inconsistent with the objectives of the present invention can be used. In some embodiments, a photoinitiator comprises an alpha-cleavage type (unimolecular decomposition process) photoinitiator or a hydrogen abstraction photosensitizer-tertiary amine synergist, operable to absorb light preferably between about 250 nm and about 400 nm or between about 300 nm and about 365 nm, to yield free radical(s).

Examples of alpha cleavage photoinitiators are Irgacure 184 (CAS 947-19-3), Irgacure 369 (CAS 119313-12-1), and Irgacure 819 (CAS 162881-26-7). An example of a photosensitizer-amine combination is Darocur BP (CAS 119-61-9) with diethylaminoethylmethacrylate. The chemical structures of some photoinitiators are provided below:

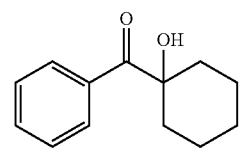

Irgacure 184

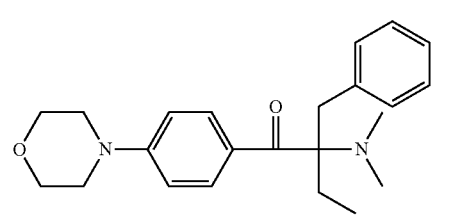

Irgacure 369

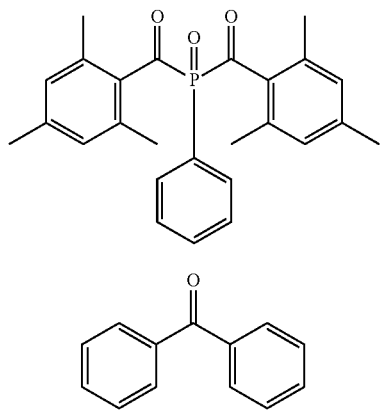

Irgacure 819

Darocure BP

In some embodiments, suitable photoinitiators comprise benzoins, including benzoin, benzoin ethers, such as benzoin methyl ether, benzoin ethyl ether and benzoin isopropyl ether, benzoin phenyl ether and benzoin acetate, acetophenones, including acetophenone, 2,2-dimethoxyacetophenone and 1,1-dichloroacetophenone, benzil, benzil ketals, such as benzil dimethyl ketal and benzil diethyl ketal, anthraquinones, including 2-methylanthraquinone, 2-ethylanthraquinone, 2-tert-butylanthraquinone, 1-chloroanthraquinone and 2-amylanthraquinone, triphenylphosphine, benzoylphosphine oxides, for example 2,4,6-trimethylbenzoyldiphenylphosphine oxide (Lucirin TPO), benzophenones, such as benzophenone and 4,4'-bis(N,N'-dimethylamino)benzophenone, thioxanthones and xanthones, acridine derivatives, phenazine derivatives, quinoxaline derivatives or 1-phenyl-1,2-propanedione, 2-O-benzoyl oxime, 1-aminophenyl ketones or 1-hydroxyphenyl ketones, such as 1-hydroxycyclohexyl phenyl ketone, phenyl 1-hydroxyisopropyl ketone and 4-isopropylphenyl 1-hydroxyisopropyl ketone.

In some embodiments, suitable photoinitiators comprise those operable for use with a HeCd laser radiation source, including acetophenones, 2,2-dialkoxybenzophenones and 1-hydroxyphenyl ketones, such as 1-hydroxycyclohexyl phenyl ketone or 2-hydroxyisopropyl phenyl ketone (=2-hydroxy-2,2-dimethylacetophenone). Additionally, in some embodiments, suitable photoinitiators comprise those operable for use with an Ar laser radiation source including benzil ketals, such as benzil dimethyl ketal. In some embodiments, a photoinitiator comprises an α-hydroxyphenyl ketone, benzil dimethyl ketal or 2,4,6 trimethylbenzoyldiphenylphosphine oxide or a mixture thereof.

Another class of suitable photoinitiators, in some embodiments, comprises ionic dye-counter ion compounds capable of absorbing actinic radiation and generating free radicals for polymerization initiation. In some embodiments, inks containing ionic dye-counter ion compounds can be cured more variably with visible light within the adjustable wavelength range of about 400 nm to about 700 nm. Ionic dye-counter ion compounds and their mode of operation are disclosed in EP-A-0 223 587 and U.S. Pat. Nos. 4,751,102; 4,772,530 and 4,772,541.

A photoinitiator can be present in an ink described herein in any amount not inconsistent with the objectives of the present invention. In some embodiments, a photoinitiator is present in an ink in an amount of up to about 5 weight percent, based on the total weight of the ink. In some embodiments, a photoinitiator is present in an amount ranging from about 0.1 weight percent to about 5 weight percent.

In some embodiments, an ink further comprises one or more sensitizers. A sensitizer can be added to an ink to increase the effectiveness of one or more photoinitiators that may also be present. Any sensitizer not inconsistent with the objectives of the present invention may be used. In some embodiments, a sensitizer comprises isopropylthioxanthone (ITX). In some embodiments, a sensitizer comprises 2-chlorothioxanthone (CTX).

A sensitizer can be present in an ink in any amount not inconsistent with the objectives of the present invention. In some embodiments, a sensitizer is present in an amount ranging from about 0.1 weight percent to about 2 weight percent, based on the total weight of the ink. A sensitizer, in some embodiments, is present in an amount ranging from about 0.5 weight percent to about 1 weight percent.

An ink, in some embodiments, further comprises one or more polymerization inhibitors or stabilizing agents. A polymerization inhibitor can be added to an ink to provide additional thermal stability to the composition. Any polymerization inhibitor not inconsistent with the objectives of the present invention may be used. In some embodiments, a polymerization inhibitor comprises methoxyhydroquinone (MEHQ). A stabilizing agent, in some embodiments, comprises one or more anti-oxidants. A stabilizing agent can comprise any anti-oxidant not inconsistent with the objectives of the present invention. In some embodiments, for example, suitable anti-oxidants include various aryl compounds, including butylated hydroxytoluene (BHT), which can also be used as a polymerization inhibitor in some embodiments described herein.

A polymerization inhibitor and/or a stabilizing agent can be present in an ink in any amount not inconsistent with the objectives of the present invention. In some embodiments, a polymerization inhibitor is present in an amount ranging from about 0.1 weight percent to about 2 weight percent, based on the total weight of the ink. A polymerization inhibitor, in some embodiments, is present in an amount ranging from about 0.5 weight percent to about 1 weight percent. In some embodiments, a stabilizing agent is present in an ink in an amount ranging from about 0.1 weight percent to about 5 weight percent or from about 0.5 weight percent to about 4 weight percent, based on the total weight of the ink. In some embodiments, a stabilizing agent is present in an amount ranging from about 1 weight percent to about 3 weight percent.

Inks described herein, in some embodiments, are not pigmented. In some embodiments, an ink is pigment-free or substantially pigment-free. In some embodiments, an ink described herein that is free or substantially free of pigment comprises less than about 5 weight percent pigment. In some embodiments, an ink that is free or substantially free of pigment comprises less than about 3 weight percent pigment or less than about 1 weight percent pigment. In some embodiments, an ink that is free or substantially free of pigment comprises less than about 0.5 weight percent pigment or less than about 0.1 weight percent pigment, based on the total weight of the ink. In some embodiments, an ink described herein does not comprise a pigment in any detectable amount and/or does not comprise any intentionally added pigment.

A pigment, in some embodiments, comprises a chemical species that can provide color and/or opacity to an ink but is not soluble in the ink. In some embodiments, a pigment can form a suspension in an ink, including a solid particle suspension. In some embodiments, a pigment comprises a solid material such as a solid powder or other particulate material. A pigment provides color to an ink, in some embodiments, by altering the light absorption or transmission profile of the ink. Further, in some embodiments, a pigment provides opacity to an ink by altering the light scattering profile of the ink. In some embodiments, a pigment comprises an inorganic pigment. Non-limiting examples of inorganic pigments include $TiO_2$ and ZnO.

Inks described herein, in some embodiments, also have a glass transition temperature ($T_g$) when cured greater than the melting point of the non-reactive wax component. The glass transition temperature can be measured according to ASTM D7028. In some embodiments, an ink described herein has a $T_g$ greater than about 75° C. when measured according to ASTM D7028. In some embodiments, an ink has a $T_g$ greater than about 85° C. or greater than about 100° C. In some embodiments, an ink has a $T_g$ between about 75° C. and about 150° C. or between about 80° C. and about 150° C. In some embodiments, an ink has a $T_g$ between about 75° C. and about 125° C. or between about 80° C. and about 125° C. when measured according to ASTM D7028. Further, the $T_g$ of an ink described herein can be altered or selected by altering one or more of the following: (a) the identity of a polymerizable component of the ink, (b) the identity of a non-reactive wax component of the ink, (c) the presence or identity of an oil in the ink, and (d) the relative amounts of the components of the ink.

Moreover, for reference purposes herein, an ink having a $T_g$ described herein when cured is an ink that includes a polymerizable component that has been at least partially polymerized and/or cross-linked. For instance, in some embodiments, a cured ink having a $T_g$ described herein is at least about 10% polymerized or cross-linked or at least about 30% polymerized or cross-linked. In some embodiments, a cured ink having a $T_g$ described herein is at least about 50%, at least about 70%, at least about 80%, or at least about 90% polymerized or cross-linked. In some embodiments, a cured ink having a $T_g$ described herein is between about 10% and about 99% or between about 20% and about 100% polymerized or cross-linked.

Inks described herein can also exhibit a variety of other desirable properties. For example, an ink described herein can have any freezing point, melting point, and/or other phase transition temperature not inconsistent with the objectives of the present invention. In some embodiments, an ink has freezing and melting points consistent with temperatures used in some 3D printing systems, including 3D printing systems designed for use with phase changing inks. In some embodiments, the freezing point of an ink is greater than about 40° C. In some embodiments, for example, an ink has a freezing point centered at a temperature ranging from about 45° C. to about 55° C. In some embodiments, an ink has a melting point centered at a temperature ranging from about 50° C. to about 80° C. In some embodiments, an ink has a freezing point below about 40° C. or below about 30° C.

In some embodiments described herein, an ink exhibits a sharp freezing point or other phase transition. In some embodiments, an ink freezes over a narrow range of temperatures. In some embodiments, an ink freezes over a temperature range of about 1° C. to about 10° C. In some embodiments, an ink freezes over a temperature range of about 1° C. to about 8° C. In some embodiments, an ink freezes over a temperature range of about 1° C. to about 5° C. In some embodiments, an ink having a sharp freezing point freezes over a temperature range of X±2.5° C., where X is the temperature at which the freezing point is centered (e.g., X=65° C.).

In addition, an ink described herein, in some embodiments, is fluid at jetting temperatures encountered in 3D printing systems. Moreover, in some embodiments, an ink solidifies once deposited on a surface during the fabrication of a three dimensionally printed article or object. Alternatively, in other embodiments, an ink remains substantially fluid upon deposition on a surface. Solidification of an ink, in some embodiments, occurs through a phase change of the ink, such as freezing. The phase change, in some embodiments, comprises a liquid to solid phase change or a liquid to semi-solid phase change. In some embodiments, solidification of an ink comprises an increase in viscosity, such as an increase in viscosity from a low viscosity state to a high viscosity state, as described further hereinbelow.

In some embodiments, an ink described herein has a viscosity profile consistent with the requirements and parameters of one or more 3D printing systems. In some embodiments, for instance, an ink described herein has a viscosity ranging from about 8.0 cP to about 14.0 cP at a temperature of about 80° C. measured according to ASTM standard D2983 (e.g., using a Brookfield Model DV-II+ Viscometer). In some embodiments, an ink has a viscosity ranging from about 9.5 cP to about 12.5 cP at a temperature of about 80° C. An ink, in some embodiments, has a viscosity ranging from about 10.5 cP to about 12.5 cP at a temperature of about 80° C. In some embodiments, an ink has a viscosity ranging from about 8.0 cP to about 10.0 cP at a temperature of about 85-87° C.

In some embodiments, an ink described herein has a viscosity ranging from about 8.0 cP to about 19.0 cP at a temperature of about 65° C. measured according to ASTM standard D2983. In some embodiments, an ink described herein has a viscosity ranging from about 8.0 cP to about 13.5 cP at a temperature of about 65° C. An ink, in some embodiments, has a viscosity ranging from about 11.0 cP to about 14.0 cP at a temperature of about 65° C. In some embodiments, an ink has a viscosity ranging from about 11.5 cP to about 13.5 cP or from about 12.0 cP to about 13.0 cP at a temperature of about 65° C.

Further, inks described herein, in some embodiments, exhibit a combination of one or more desirable features. In some embodiments, for instance, an ink in the non-cured state has one or more of the following properties:

1. Freezing point between about 30° C. and about 65° C.;
2. Jetting viscosity of about 8 cP to about 16 cP at 70-95° C.; and
3. Thermal stability for at least 3 days at the jetting temperature.

Viscosity can be measured according to ASTM D2983 (e.g., using a Brookfield Model DV-II+ Viscometer). In addition, for reference purposes herein, a thermally stable material exhibits no greater than about a 35 percent change in viscosity over a specified time period (e.g., 3 days) when measured at the specified temperature (e.g., a jetting temperature of 85° C.) at the beginning and at the end of the time period. In some embodiments, the viscosity change is no greater than about 30 percent or no greater than about 20 percent. In some embodiments, the viscosity change is between about 10 percent and about 20 percent or between about 25 percent and about 30 percent. Moreover, in some embodiments, the change in viscosity is an increase in viscosity.

Moreover, an ink described herein in a cured state, in some embodiments, can exhibit one or more desired properties. An ink in a cured state, in some embodiments, comprises an ink that includes a polymerizable component that has been at least partially polymerized and/or cross-linked. For instance, in some embodiments, a cured ink is at least about 10% polymerized or cross-linked or at least about 30% polymerized or cross-linked. In some embodiments, a cured ink is at least about 50%, at least about 70%, at least about 80%, or at least about 90% polymerized or cross-linked. In some embodiments, a cured ink is between about 10% and about 99% polymerized or cross-linked.

In some embodiments, an ink described herein can have one or more of the following properties in a cured state:

1. $T_g$ between about 80° C. and about 150° C. (as measured by ASTM D7028);
2. Tensile strength of at least about 35 MPa (as measured by ASTM D 638);
3. Tensile modulus of at least about 1380 MPa (as measured by ASTM D 638);
4. Break elongation of at least about 5% (as measured by ASTM D 638);
5. Hardness of at least about 60 shore D (as measured by ASTM D 2240);
6. Impact strength of at least about 0.2 ft-lb/in (107 N-cm/cm) (Izod notched, as measured by ASTM D 256);
7. Flexural strength of at least about 10 MPa (as measured by ASTM D 638); and
8. Flexural modulus of at least about 17 MPa (as measured by ASTM D 792).

Further, in some embodiments, an ink described herein is opaque at room temperature (about 25° C.) when cured. An ink described herein can therefore be used to provide printed articles that are opaque at room temperature, in some embodiments. In some embodiments, an ink is opaque above the melting point of the non-reactive wax component of the ink and remains opaque when cooled below the melting point of the non-reactive wax component. Moreover, the opacity of a cured ink at room temperature can be obtained and/or increased, in some embodiments, by heating the cured ink to a temperature above the melting point of the non-reactive wax component and subsequently cooling the ink to a temperature below the melting point of the non-reactive ink.

An opaque ink or printed article, in some embodiments, comprises an ink or article that transmits no more than about 10% of incident light over a 1 centimeter (cm) path length. In some embodiments, an opaque ink or article transmits no more than about 20% or no more than about 30% of incident light over a 1 cm path length. In some embodiments, an opaque ink or article transmits less than about 5% of incident light over a 1 cm path length. Incident light, in some embodiments, comprises visible light. In some embodiments, the incident light comprises electromagnetic radiation having a wavelength from about 450 nm to about 500 nm, from about 450 nm to about 550 nm, from about 500 nm to about 570 nm, from about 500 nm to about 600 nm, from about 600 nm to about 650 nm, from about 600 nm to about 700 nm, or from about 650 nm to about 750 nm.

Opaque inks and printed articles described herein, in some embodiments, can be used for various applications, such as dental modeling applications. In some embodiments, an opaque ink or printed article comprises an ink or article that can be detected and/or measured with a dental laser scanner with the same or substantially the same accuracy as an otherwise similar plaster material or plaster article. A non-limiting example of a dental laser scanner is the 3Shape D700 dental scanner, commercially available from CadBlu Dental. Further, in some embodiments, an opaque ink or printed article can be visualized and/or scanned with the same or substantially the same accuracy as an otherwise similar plaster material or plaster article, without the use of a contrast powder to coat or dust the ink or printed article.

Inks described herein, in some embodiments, can be produced in any manner not inconsistent with the objectives of the present invention. In some embodiments, for instance, a method for the preparation of an ink described herein comprises the steps of mixing the polymerizable component and the non-reactive wax component, melting the mixture, and filtering the molten mixture. Melting the mixture, in some embodiments, is carried out at a temperature of about 75° C. or in a range from about 75° C. to about 85° C. In addition, in some embodiments, one or more other components, such as an oil described herein, are also mixed with the polymerizable component and the non-reactive wax component. In some embodiments, an ink described herein is produced by placing all components of the ink in a reaction vessel and heating the resulting mixture to a temperature ranging from about 75° C. to about 85° C. with stirring. The heating and stirring are continued until the mixture attains a substantially homogenized molten state. The molten mixture is filtered while in a flowable state to remove any large undesirable particles that may interfere with jetting. The filtered mixture is then cooled to ambient temperatures until it is heated in the ink jet printer.

II. Compositions Comprising a 3D Printed Article

In another aspect, compositions comprising 3D printed articles or objects are described herein. In some embodiments, a composition comprises a three dimensionally printed article comprising an ink, the ink comprising about 10-95 weight % polymerizable component and about 3-25 weight % non-reactive wax component, based on the total weight of the ink. In some embodiments, the ink when cured has a $T_g$ greater than the melting point of the non-reactive wax component. In addition, in some embodiments, the ink further comprises about 1-10 weight % oil. Any ink described hereinabove in Section I may be used. For example, an ink of a composition described herein can comprise any combination of polymerizable components, non-reactive wax components, and/or other additives described herein not inconsistent with the objectives of the present invention. In some embodiments, for instance, an ink further comprises an oil. In some embodiments, an ink further comprises at least one dye. Moreover, in some embodiments, an ink is not pigmented.

Therefore, in some embodiments, an article can be obtained by curing an ink described herein, such as an ink comprising about 10-95 weight % polymerizable component, about 3-25 weight % non-reactive wax component, and about 1-10 weight % oil. Further, in some embodiments, the $T_g$ of the cured ink is greater than the melting point of the non-reactive wax component. Moreover, in some embodiments, an article obtained by curing an ink described herein exhibits one or more of the following properties:

1. $T_g$ between about 80° C. and about 150° C. (as measured by ASTM D7028);
2. Tensile strength of at least about 35 MPa (as measured by ASTM D 638);
3. Tensile modulus of at least about 1380 MPa (as measured by ASTM D 638);
4. Break elongation of at least about 5% (as measured by ASTM D 638);
5. Hardness of at least about 60 shore D (as measured by ASTM D 2240);
6. Impact strength of at least about 0.2 ft-lb/in (10.7 N-cm/cm) (Izod notched, as measured by ASTM D 256);

7. Flexural strength of at least about 10 MPa (as measured by ASTM D 638); and

8. Flexural modulus of at least about 17 MPa (as measured by ASTM D 792).

Further, in some embodiments, a three dimensionally printed article of a composition described herein is opaque at room temperature when cured, as described herein.

In addition, in some embodiments, a 3D printed article of a composition described herein further comprises a support material. A support material can be used to support at least one layer of an ink during the 3D printing process. In some embodiments, a 3D printed article described herein comprises a plurality of layers of the ink, wherein the layers of the ink are deposited according to data in a computer readable format. In some embodiments, at least one of the deposited layers of ink is supported by a support material. In some embodiments, the support material is removable to complete production of the 3D printed article or object.

III. Methods of Printing a 3D Article

In another aspect, methods of printing a 3D article or object are described herein. In some embodiments, a method of printing a 3D article comprises selectively depositing layers of a fluid ink to form the three dimensional article on a substrate, the ink comprising about 10-95 weight % polymerizable component and about 3-25 weight % non-reactive wax component. In some embodiments, the ink when cured has a $T_g$ greater than the melting point of the non-reactive wax component. In addition, in some embodiments, the ink further comprises about 1-10 weight % oil. Any ink described hereinabove in Section I may be used.

In some embodiments, the layers of the ink are deposited according to an image of the three dimensional article in a computer readable format. In some embodiments, the ink is deposited according to preselected computer aided design (CAD) parameters.

In some embodiments, a method of printing a 3D article further comprises supporting at least one of the layers of the ink with a support material. Any support material not inconsistent with the objectives of the present invention may be used.

In some embodiments, a method of printing a 3D article further comprises curing the ink. In some embodiments, a method of printing a 3D article further comprises subjecting the ink to electromagnetic radiation of sufficient wavelength and intensity to cure the ink, where curing can comprise polymerizing one or more polymerizable functional groups of one or more components of the ink. In some embodiments of printing a 3D article, a layer of deposited ink is cured prior to the deposition of another or adjacent layer of ink. Thus, in some embodiments, an article such as an article described hereinabove in Section II can be obtained by a method described herein. For example, in some embodiments, a dental model is prepared by a method described herein using an ink described herein.

In some embodiments, a method described herein further comprises heating the three dimensional article to a temperature above the melting point of the non-reactive wax component of the article. In some embodiments, a method described herein further comprises heating the three dimensional article to 75° C. or above. In some embodiments, the article is heated to 85° C. or above or 100° C. or above. In some embodiments, the article is heated to a temperature between about 75° C. and about 150° C. or between about 80° C. and about 150° C. In some embodiments, the article is heated to a temperature between about 75° C. and about 125° C. or between about 80° C. and about 125° C.

Moreover, in some embodiments, a method described herein further comprises cooling the three dimensional article to room temperature (about 25° C.). In some embodiments, cooling is carried out rapidly. For example, in some embodiments, an article is cooled to room temperature within about 5 minutes or less. In some embodiments, an article is cooled to room temperature within about 1 minute or less. In some embodiments, an article is cooled to room temperature within about 30 seconds or less, within about 10 seconds or less, or within about 5 seconds or less.

Cooling, including rapid cooling, can be carried out in any manner not inconsistent with the objectives of the present invention. In some embodiments, for example, cooling comprises placing the article in a refrigerator. In some embodiments, cooling comprises placing the article in a freezer. In some embodiments, cooling comprises at least partially immersing the article in a cooled liquid. In some embodiments, an article is completely immersed in a cooled liquid. A cooled liquid, in some embodiments, has a temperature between about −90° C. and about 25° C. or between about −70° C. and about −10° C. In some embodiments, a cooled liquid has a temperature between about −30° C. and about 0° C., between about 0° C. and about 25° C., between about 0° C. and about 15° C. or between about 0° C. and about 10° C. Any liquid not inconsistent with the objectives of the present invention may be used. In some embodiments, a liquid comprises an aqueous liquid. In other embodiments, a liquid comprises an organic liquid. In some embodiments, a liquid comprises water, isopropyl alcohol, acetone, or a combination thereof.

In some embodiments, a preselected amount of ink described herein is heated to the appropriate temperature and jetted through the print head or a plurality of print heads of a suitable inkjet printer to form a layer on a print pad in a print chamber. In some embodiments, each layer of ink is deposited according to the preselected CAD parameters. A suitable print head to deposit the ink, in some embodiments, is the piezoelectric 2850 print head available from Xerox Corporation's Office Products Business Unit in Wilsonville, Oreg. Additional suitable print heads for the deposition of ink and support material described herein are commercially available from a variety of ink jet printing apparatus manufacturers. For example, the Taipan print head available from Xerox or Ricoh print heads may also be used in some embodiments.

In some embodiments comprising a method of printing a 3D article comprising an ink as described herein, the ink remains substantially fluid upon deposition. In other embodiments, the ink exhibits a phase change upon deposition and/or solidifies upon deposition. In some embodiments, the temperature of the printing environment can be controlled so that the jetted droplets of ink solidify on contact with the receiving surface. In other embodiments, the jetted droplets of ink do not solidify on contact with the receiving surface, remaining in a substantially fluid state. In some embodiments, after each layer is deposited, the deposited material is planarized and cured with electromagnetic (e.g., UV) radiation prior to the deposition of the next layer. Optionally, several layers can be deposited before planarization and curing, or multiple layers can be deposited and cured followed by one or more layers being deposited and then planarized without curing. Planarization corrects the thickness of one or more layers prior to curing the material by evening the dispensed material to remove excess material and create a uniformly smooth exposed or flat up-facing surface on the support platform of the printer. In some embodiments, planarization is accomplished with a wiper device, such as a roller, which may be counter-rotating in one or more printing directions but not counter-rotating in one or more other printing directions. In some embodiments, the wiper device comprises a roller and a wiper that removes excess material from the roller. In some embodiments, the wiper device is heated. It should be noted that the consistency of the jetted ink described herein prior to curing, in some embodiments, must be sufficient to retain its shape and not be subject to excessive viscous drag from the planarizer.

Moreover, a support material, in some embodiments, can be deposited in a manner consistent with that described herein for the ink. The support material, for example, can be deposited according to the preselected CAD parameters such that the support material is adjacent or continuous with one or more layers of the ink. Jetted droplets of the support material, in some embodiments, solidify or freeze on contact with the receiving surface. In some embodiments, the deposited support material is also subjected to planarization.

Layered deposition of the ink and support material can be repeated until the 3D article has been formed. In some embodiments, a method of printing a 3D article further comprises removing the support material from the ink.

Some embodiments described herein are further illustrated in the following non-limiting examples.

Example 1

Opaque Ink

An ink according to one embodiment described herein was provided in accordance with the formulation of Table I. The weight percents of Table I are based on the total weight of the ink.

TABLE I

| Ink 1 | |
|---|---|
| Component | Amount (Wt. %) |
| Polymerizable Component[1] | 86.00 |
| Non-Reactive Wax Component[2] | 6.04 |
| Oil[3] | 3.84 |
| Photoinitiator[4] | 4.05 |
| Inhibitor[5] | 0.07 |
| Total | 100 |

[1]Mixture of BR-741 (31.26%) and SR 205 (54.74%), where weight percents are based on the total weight of the ink - Bomar Specialties Co., Winsted, CT, and SARTOMER Company, Exton, PA, respectively.
[2]Mixture of C10, C12, C16, and C18 urethane waxes - Hampford Research, Inc., Stratford, CT.
[3]Corn oil - Wal-Mart Stores, Inc.
[4]Mixture of Irgacure 184 (3.89%) and Irgacure 819 (0.16%), where weight percents are based on the total weight of the ink - Ciba Specialty Chemicals, Inc. (BASF), Basel, Switzerland
[5]BHT - Chemtura Corp. Middlebury, CT.

The polymerizable component (2688.26 grams), non-reactive wax component (188.93 grams), oil (120 grams), photoinitiator (126.46 grams), and inhibitor (2.2 grams) were charged into a vessel equipped with mechanical stirring and a heating unit. The mixture was then heated to about 80° C.-90° C. After the mixture was melted, stirring was begun, and the mixture was blended for about 1-2 hours at 80° C.-90° C. The liquid was then filtered with a 1 micron filter to remove solid particles. The ink provided in Table I had a viscosity of 10 cP at a temperature of 85° C. (Brookfield Model DV-II+ Viscometer).

The resulting ink was jetted at about 65° C.-68° C. through a Projet™ 3000 System from 3D Systems using a Xerox Z 850 print head to form three dimensional parts. The cured ink exhibited a tensile modulus of 1800 MPa when tested according to ASTM D 638, a break elongation of 10% when tested according to ASTM D 638, and a tensile strength of 38 MPa when tested according to ASTM D 638.

Example 2

Opaque Ink

An ink according to one embodiment described herein was provided in accordance with the formulation of Table II. The weight percents of Table II are based on the total weight of the ink.

TABLE II

| Ink 2 | |
|---|---|
| Component | Amount (Wt. %) |
| Polymerizable Component[6] | 89.44 |
| Non-Reactive Wax Component[7] | 6.29 |
| Photoinitiator[8] | 4.21 |
| Inhibitor[9] | 0.07 |
| Total | 100 |

[6]Mixture of BR-741 (32.51%) and SR 205 (56.93%), where weight percents are based on the total weight of the ink - Bomar Specialties Co., Winsted, CT, and SARTOMER Company, Exton, PA, respectively.
[7]Mixture of C10, C12, C16, and C18 urethane waxes - Hampford Research, Inc., Stratford, CT.
[8]Mixture of Irgacure 184 (4.04%) and Irgacure 819 (0.17%), where weight percents are based on the total weight of the ink - Ciba Specialty Chemicals, Inc. (BASF), Basel, Switzerland.
[9]BHT - Chemtura Corp. Middlebury, CT.

The polymerizable component (2688.26 grams), non-reactive wax component (188.93 grams), photoinitiator (126.46 grams), and inhibitor (2.2 grams) were charged into a vessel equipped with mechanical stirring and a heating unit. The mixture was then heated to about 80° C.-90° C. After the mixture was melted, stirring was begun, and the mixture was blended for about 1-2 hours at 80° C.-90° C. The liquid was then filtered with a 1 micron filter to remove solid particles. The ink provided in Table II had a viscosity of 11 cP at a temperature of 85° C. (measured with a Brookfield Model DV-II+Viscometer).

The resulting ink was jetted at about 65° C.-68° C. through a Projet™ 3000 System from 3D Systems using a Xerox Z 850 print head to form three dimensional parts. The cured ink exhibited a tensile modulus of 1880 MPa when tested according to ASTM D 638, a break elongation of 12% when tested according to ASTM D 638, and a tensile strength of 40 MPa when tested according to ASTM D 638.

Example 3

Optical Scanning of 3D Printed Articles

Figure 2:
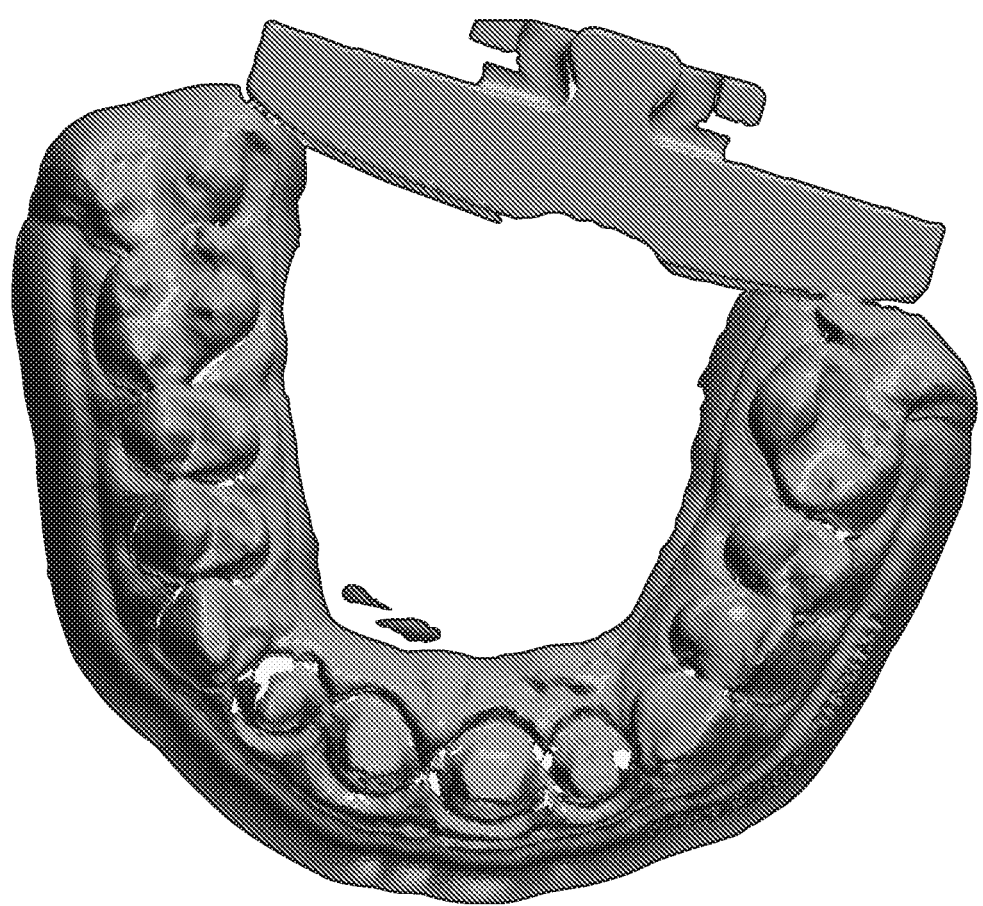
FIG. 2 illustrates the optical scanning properties of a printed article formed from an ink according to an embodiment described herein.

Three dimensional printed articles were prepared using the ink of Example 1 as well as an ink not according to an embodiment described herein. The same CAD file was used to prepare both printed articles. Both printed articles comprised a dental model. Following printing, each printed article was heated to above 75° C. and subsequently cooled to room temperature (about 25° C.). Next, each printed article was scanned by a dental laser scanner (3Shape D700 Scanner, Cadblu Dental, Inc.) using the same scanning parameters. FIG. 1 illustrates the result of the scan of the printed article formed from an ink not according to an embodiment described herein. FIG. 2 illustrates the result of the scan of the printed article formed from the ink of Example 1. As shown by FIGS. 1 and 2, the article formed from the ink of Example 1 provided a printed part that could be accurately detected and measured by the dental scanner.

All patent documents referred to herein are incorporated by reference in their entireties. Various embodiments of the invention have been described in fulfillment of the various objectives of the invention. It should be recognized that these embodiments are merely illustrative of the principles of the present invention. Numerous modifications and adaptations thereof will be readily apparent to those skilled in the art without departing from the spirit and scope of the invention.

That which is claimed:

1. An ink for use in a three dimensional printing system comprising:
   about 10-95 weight % polymerizable component; and
   about 3-25 weight % non-reactive wax component,
   wherein the ink when cured has a $T_g$ greater than the melting point of the non-reactive wax component; and
   wherein the $T_g$ is between 75° C. and 150° C.

2. The ink of claim 1 further comprising an oil.

3. The ink of claim 2, wherein the oil comprises about 1-10 weight % of the ink.

4. The ink of claim 2, wherein the oil comprises a plant oil.

5. The ink of claim 1 further comprising at least one dye.

6. The ink of claim 1 further comprising one or more additives selected from the group consisting of photoinitiators, inhibitors, stabilizing agents, sensitizers, and combinations thereof.

7. The ink of claim 1, wherein the ink is not pigmented.

8. The ink of claim 1, wherein the ink does not comprise an inorganic pigment.

9. The ink of claim 7, wherein the ink is opaque at about 25° C. when cured.

10. The ink of claim 1, wherein the polymerizable component comprises one or more species of (meth)acrylates.

11. The ink of claim 1, wherein the non-reactive wax component comprises an SPC wax.

12. A three dimensionally printed dental model comprising an ink, the ink comprising about 10-95 weight % polymerizable component and about 3-25 weight % non-reactive wax component, wherein the ink when cured has a $T_g$ greater than the melting point of the non-reactive wax component, wherein the $T_g$ is between 75° C. and 150° C., and wherein the ink is not pigmented.

13. A method of printing a three dimensional article comprising:
   selectively depositing layers of a fluid ink to form the three dimensional article on a substrate, the ink comprising about 10-95 weight % polymerizable component and about 3-25 weight % non-reactive wax component, wherein the ink when cured has a $T_g$ greater than the melting point of the non-reactive wax component, and wherein the $T_g$ is between 75° C. and 150° C.

14. The method of claim 13, wherein the layers of the ink are deposited according to an image of the three dimensional article in a computer readable format.

15. The method of claim 13 further comprising supporting at least one of the layers of the ink with a support material.

16. The method of claim 13 further comprising curing the layers of ink.

17. The method of claim 13 further comprising heating the three dimensional article to a temperature greater than the melting point of the non-reactive wax component.

18. The method of claim 17 further comprising cooling the three dimensional article to about 25° C.

19. The method of claim 18, wherein cooling is carried out within about 5 minutes or less.

20. The method of claim 18, wherein cooling comprises at least partially immersing the three dimensional article in a cooled liquid at a temperature between about −90° C. and about 25° C. or placing the three dimensional article in a refrigerator.

* * * * *